(12) United States Patent
Vijaya Kumar et al.

(10) Patent No.: US 8,975,402 B2
(45) Date of Patent: Mar. 10, 2015

(54) HPLC METHOD FOR THE ANALYSIS OF BOSETAN AND RELATED SUBSTANCES AND USE OF THESE SUBSTANCES AS REFERENCE STANDARDS AND MARKERS

(75) Inventors: Erra Koteswara Satya Vijaya Kumar, Maharashtra (IN); Avinash Prabhakar Nikam, Maharashtra (IN)

(73) Assignee: Generics [UK] Limited, Herforshire (GB)

( * ) Notice: Subject to any disclaimer, the term of this patent is extended or adjusted under 35 U.S.C. 154(b) by 122 days.

(21) Appl. No.: 13/126,332

(22) PCT Filed: Nov. 2, 2009

(86) PCT No.: PCT/GB2009/051474
§ 371 (c)(1),
(2), (4) Date: Jul. 8, 2011

(87) PCT Pub. No.: WO2010/061210
PCT Pub. Date: Jun. 3, 2010

(65) Prior Publication Data
US 2011/0263853 A1    Oct. 27, 2011

(30) Foreign Application Priority Data
Nov. 3, 2008 (IN) .............................. 1871/KOL/2008

(51) Int. Cl.
*C07D 239/52* (2006.01)
(52) U.S. Cl.
CPC .................................... *C07D 239/52* (2013.01)
USPC .......................................................... 544/296
(58) Field of Classification Search
CPC ..................................................... C07D 239/52

USPC .......................................................... 544/296
See application file for complete search history.

(56) References Cited

U.S. PATENT DOCUMENTS

| 5,292,740 | A | 3/1994 | Burri et al. |
| 5,739,333 | A | 4/1998 | Yamada et al. |
| 6,136,971 | A | 10/2000 | Harrington et al. |
| 6,479,692 | B1 | 11/2002 | Ekwuribe et al. |
| 8,288,401 | B2 | 10/2012 | Gaitonde et al. |
| 2008/0188663 | A1 | 8/2008 | Kumar et al. |
| 2008/0242687 | A1 | 10/2008 | Gant et al. |
| 2009/0156811 | A1 | 6/2009 | Taddei et al. |
| 2009/0291974 | A1 | 11/2009 | Zhu |
| 2010/0261742 | A1 | 10/2010 | Gaitonde et al. |
| 2010/0331352 | A1 | 12/2010 | Gaitonde et al. |

(Continued)

FOREIGN PATENT DOCUMENTS

| CA | 2 071 193 | 5/1992 |
| CA | 2646795 | 6/2009 |
| CN | 1 425 007 | 6/2003 |

(Continued)

OTHER PUBLICATIONS

Hopfgartner et al. (Journal of Mass Spectrometry, vol. 31, 69-76 (1996).*

(Continued)

*Primary Examiner* — Kristin Vajda
*Assistant Examiner* — Valerie Rodriguez-Garcia

(57) ABSTRACT

The present invention relates to a new HPLC method for the analysis of the drug substance bosentan and related substances and to the use of said substances as reference standards and markers.

5 Claims, 7 Drawing Sheets

(56) References Cited

U.S. PATENT DOCUMENTS

| | | | |
|---|---|---|---|
| 2011/0014291 | A1 | 1/2011 | Dixit et al. |
| 2012/0041200 | A1 | 2/2012 | Biffi et al. |

FOREIGN PATENT DOCUMENTS

| | | | |
|---|---|---|---|
| CN | 101175484 | A | 5/2008 |
| EP | 0 526 708 | | 2/1993 |
| EP | 0 526 708 | A1 | 2/1993 |
| EP | 0 526 708 | B1 | 2/1993 |
| EP | 0 743 307 | B1 | 9/2001 |
| EP | 2 072 503 | | 6/2009 |
| IN | 1245/MUM/2007 | | 6/2007 |
| WO | WO 01/36384 | | 5/2001 |
| WO | WO 01/43742 | | 6/2001 |
| WO | WO 01/55120 | A1 | 8/2001 |
| WO | WO 2004/076443 | | 9/2004 |
| WO | WO 2004/081016 | | 9/2004 |
| WO | WO 2004/087660 | | 10/2004 |
| WO | WO 2006123285 | A2 | 11/2006 |
| WO | WO 2008/135795 | | 11/2008 |
| WO | WO 2009/004374 | | 1/2009 |
| WO | WO 2009004374 | * | 1/2009 |
| WO | WO 2009/047637 | | 4/2009 |
| WO | WO 2009/053748 | | 4/2009 |
| WO | WO 2009/093127 | | 7/2009 |
| WO | WO 2009/095933 | | 8/2009 |
| WO | WO 2009/098517 | | 8/2009 |
| WO | WO 2009/112954 | | 9/2009 |
| WO | WO 2010/061210 | | 6/2010 |

OTHER PUBLICATIONS

Metabolite Services at JIC—http://www.jic.ac.uk/services/metabolomics/topics/lcms/why.htm—Mar. 8, 2009.*
Hopfgartner G. et al., "Exact mass measurement of product ions for the structural elucidation of drug metabolites with a tandem quadrupole orthogonal-acceleration time-of-flight mass spectrometer", Journal of the American Society for Mass Spectrometry, Elsevier Science Inc., US, vol. 10, No. 12, Dec. 1, 1999, pp. 1305-1314.
Hopfgartner G. et al., "Fragmentation of Bosentan ( Ro 47-0203) in ion-spray mass spectrometry after collision-induced dissociation at low energy: a case of radical fragmentation of an even-electron ion", Journal of Mass Sepctrometry, Wiley, Chichester, GB, vol. 31, Jan. 1, 1996, pp. 69-76.
Lausecker B. et al., "Simultaneous determination of bosetan and its three major metabolites in various biological matrices and species using narrow bore liquid chromatography with ion spray tandem mass spectrometric detection", Journal of Chromatography B: Biomedical Applications, Elsevier Science Publishers, NL, vol. 749, No. 1, Nov. 10, 2000, pp. 67-83.
Dell D. et al., "Evolving bipanalytical methods for the cardiovascular drug bosentan", Chromatographia, Wiesbaden, DE, vol. 55, No. Suppl, Jan. 1, 2002, pp. 115-119.
Lausecker B. et al., "Determination of an endothelin receptor antagonist in human plasma by narrow-bore liquid chromatography and ionspray tandem mass spectrometry", Journal of Chromatography, Elsevier Science Publishers B.V., NL, vol. 712, No. 1, Sep. 29, 1995, pp. 75-83.
Harrington Peter J. et al., "Research and Development of a Second Generation Process for Bosentan", Organic Process Research and Development, Cambridge, GB, vol. 6, Jan. 1, 2002, pp. 120-124.

International Search Report PCT/GB2009/051474 dated Feb. 19, 2010 (5 pgs.).
T.W. Greeene & P.G.M. Wuts, Protective Groups in Organic Synthesis (3rd Ed., John Wily & Sons, 1999) re hydroxyl protection.
UC Santa Barbara, Materials Research Laboratory; MDSC Manual; http://www.mrl.ucsb.edu/sites/default/files/mrl_docs/instruments/MDSCManual.pdf.
Uses of X-ray Powder Diffraction in the Pharmaceutical Industry; in Pharmaceutical Sciences Encyclopedia: Drug Discovery, Development, and Manufacturing, Edited by Shayne C. Gad, John Wiley & Sons, 2010.
X-ray diffraction; in US Pharmacopeia 29, Chapter 941.
Poupaert, Encyclopedia of pharmaceutical technology, 2007, pp. 1362-1369.
J Keith Gnillory Drugs and Pharmaceutical Sciences Chapter 5, 1999.
Lei-Shu Wu, et al, Journal Pharmaceutical Sciences, vol. 83, No. 10, Oct. 1994, pp. 1404-1406.
Martinez-Oharriz, et al., Pharma Science 199, vol. 83(2), 174-177.
Swanepol, et al. European J. of Pharmaceutics and Biopharmaceutics, 2003, No. 55, pp. 345-349.
Newport Premium Report, Bosentan monohydrate, downloaded Sep. 4, 2013, 2 pages.
Background Information for the Oct. 2002 ACPS Meeting. Scientific Considerations of Polymorphism in Pharmaceutical Solids: Abbreviated New Drug Applications.
Bioorganic & Medicinal Chemistry, vol. 9, 2001, pp. 2955-2968.
Boss, et al., "Bis-sulfonamides as Endothelin Receptor Antagonists", Bioorganic & Medicinal Chemistry Letters, No. 13, 2003, 951-954.
Bosentan Wikipedia extract 26.6.08.
Chemblink webpage re 4,6-dichloro-5-(2-methoxyphenoxy)-2,2'-bipyrimidine 19.1.09.
Chemburkar et al., Organic Process Research & Development, vol. 4, 2000, pp. 413-417.
Chinese Journal of Medicinal Chemistry, vol. 15, 2005, pp. 230-233.
Comprehensive Heterocyclic Chemistry, vol. 3, 1984, pp. 98-101 and 134.
Dunitz et al., Acc. Chem. Res., vol. 28, 1995, pp. 193-200.
EMEA 2005.
Heterocyclic Compounds—The Pyrimidines, 1994, XP-002495603, pp. 397-401.
J.K. Guillory, Generation of Polymorphs, Hydrates, Solvates and Amorphous Solids, in Polymorphism in Pharmaceutical Solids, pp. 183-226 (H.G. Brittain ed. 1999).
J. Lang, Application Note, Thermal Analysis, Perkin Elmer, 2010.
Martinez-Oharriz et al., Journal of Pharmaceutical Sciences, 1994, vol. 83(2), pp. 174-177.
Modern Drug Discovery, Mar. 2000, p. 53, K. Knapman.
Neidhard W. et al., Chimia, vol. 50, 1996, pp. 519-524.
"Protection of a reactive group" IUPAC Gold Book 2011.
S.L. Morisette et al., Advanced Drug Delivery Reviews, vol. 56, 2004, pp. 275-300.
S.R. Vippagunta et al., Advanced Drug Delivery Reviews, vol. 48, 2001, pp. 3-26.
Topics in Current Chemistry, vol. 198, 1998, pp. 163-208.
Joel Bernstein, Table 4.6, Polymorphism in Molecular Crystals, Clarendon Press, Oxford, 2002, 3 pages.
Metabolite Services at JIC, Mar. 8, 2009, 2 pages, www.jic.ac.uk/services/metabolomics/topics/lcms/why.htm.

* cited by examiner

Impurity A

Impurity B

Impurity C

Impurity D

Impurity E

HPLC METHOD FOR THE ANALYSIS OF BOSETAN AND RELATED SUBSTANCES AND USE OF THESE SUBSTANCES AS REFERENCE STANDARDS AND MARKERS

CROSS-REFERENCE TO RELATED APPLICATION(s)

This application is a Section 371 National Stage Application of International No. PCT/GB2009/051474, filed 2 Nov. 2009 and published as WO 2009/051474 A1 on 3 Jun. 2010, which claims priority from the IN Patent Application No. 1871/KOL/2008, filed 3 Nov. 2008, the contents of which are incorporated herein in their entirety for all purposes.

FIELD OF THE INVENTION

The present invention relates to a new HPLC method for the analysis of the drug substance bosentan and related substances and to the use of said substances as reference standards and markers.

BACKGROUND ART

In order to secure marketing approval for a pharmaceutical product, a manufacturer must submit detailed evidence to the appropriate regulatory authorities to prove that the product is suitable for release on to the market. It is therefore necessary to satisfy regulatory authorities that the product is acceptable for administration to humans and that the particular pharmaceutical composition, which is to be marketed, is free from impurities at the time of release and that it has acceptable storage stability.

Submissions to regulatory authorities must include analytical data which demonstrate that impurities are absent from the active pharmaceutical ingredient (API) at the time of manufacture, or are present at acceptable levels, and that the storage stability of the pharmaceutical composition is acceptable.

The likely impurities in APIs and pharmaceutical compositions include residual quantities of synthetic precursors (intermediates), by-products which arise during the synthesis of the API, residual solvents, isomers of the API (e.g. geometrical isomers, diastereomers or enantiomers), contaminants which are present in materials used in the synthesis of the API or in the preparation of the pharmaceutical composition, and unidentified adventitious substances. Other impurities which may appear during storage include degradants of the API, such as those formed by hydrolysis or oxidation.

The health authorities have very stringent standards and manufacturers must demonstrate that their product is relatively free from impurities or within acceptable limits and that these standards are reproducible for each batch of pharmaceutical product that is produced.

The tests required to demonstrate that the API or pharmaceutical compositions are safe and effective include purity assays, related substances testing, content uniformity testing and dissolution testing. The assay test determines the purity of the test product when compared to a standard of known purity, while the related substances test is used to quantify all the impurities present in the product. The content uniformity test ensures that batches of product like a tablet contain a uniform amount of API and the dissolution test ensures that each batch of product has a consistent dissolution and release of the API.

The technique of choice for the analysis of the API or pharmaceutical compositions (e.g. tablets and capsules) is usually High Performance Liquid Chromatography (HPLC) coupled with a detector. Detectors include UV-visible detectors or mass-spectrometry (MS) detectors. The API and the impurities present, if any, are separated on the HPLC stationary phase and they can be detected and quantified by said detectors.

HPLC is a chromatographic separation technique in which high pressure pumps force the substance or mixture being analysed together with a liquid solvent-mobile phase, also referred to as the eluant—through a separating column containing the stationary phase.

HPLC analysis may be performed in isocratic or gradient mode. In isocratic mode, the mobile phase composition is constant throughout. A gradient HPLC separation is carried out by a gradual change over a period of time in the percentage of the two or more solvents making up the mobile phase. The change in solvent is controlled by a mixer which mixes the solvents to produce the mobile phase prior to its passing through the column.

If a substance interacts strongly with the stationary phase, it remains in the column for a relatively long time, whereas a substance that does not interact with the stationary phase as strongly elutes out of the column sooner. Depending on the strength of interactions, the various constituents of the analyte appear at the end of the separating column at different times, known as retention times, where they can be detected and quantified by means of a suitable detector, such as a UV detector.

Bosentan belongs to a class of highly substituted pyrimidines and is used for the treatment of pulmonary arterial hypertension by blocking the action of endothelin.

Bosentan, having a chemical structure as shown in formula (I), has a molecular weight of 551.615 and its molecular formula is $C_{27}H_{29}N_5O_6S$. Bosentan is a white to yellowish white powder and is freely soluble in acetonitrile.

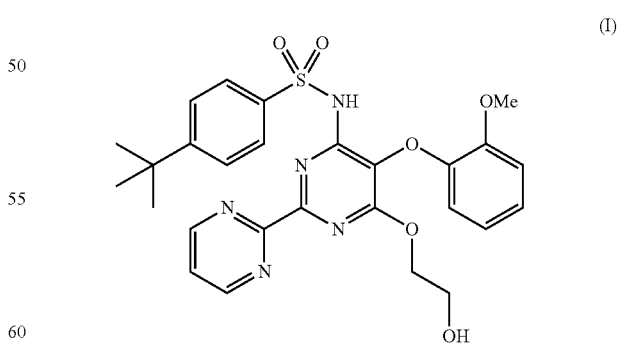

(I)

The prior art discloses three process impurities, Ro 47-0005, Ro 47-4056 and Ro 47-9931, obtained during the synthesis of bosentan (EMEA 2005). However, the structures of these impurities were not described. Further, the report also described the formation of three metabolites: Ro 48-5033

(hydroxylation product of the tertiary butyl group), Ro 47-8634 (free phenol metabolite) and Ro 64-1056 (a secondary metabolite, which is free phenol and has a hydroxylated tertiary butyl group).

Several HPLC methods to detect these impurities are reported in the literature, for example: (1) "Evolving Bioanalytical Methods for the Cardiovascular Drug Bosentan", Chromatographia, vol. 55, pages S115-S119, 2002; and (2) "Determination of an endothelin receptor antagonist in human plasma by narrow-bore liquid chromatography and ionspray tandem mass spectrometry", J. Chromatography A, vol. 712, pages 75-83, 1995. These publications describe isocratic HPLC methods using mixtures of ammonium acetate and acetonitrile and reverse phase chromatography (RP-18 or RP-8).

However, none of the current HPLC methods are suitable for the detection and quantification of all synthetic intermediates and other related substances that are present in a bosentan sample, particularly a sample synthesised by alternative novel routes, such as the route disclosed in WO 2009/004374 and its priority application IN 1245/MUM/2007. Current methods are also deficient in estimating the total impurities in bosentan and its salts.

Therefore the HPLC methods reported in the prior art are not convenient or suitable for analysing bosentan and its salts as an API, particularly with respect to related substances present in a sample synthesised by the route disclosed in WO 2009/004374 and its priority application IN 1245/MUM/2007.

Consequently, although several HPLC methods have been reported in the literature for the analysis of bosentan and/or its salts and its impurities, there is still a need for an alternative method which avoids the problems associated with the known methods as discussed above.

Studies by the present inventors have lead to the development and validation of a new, efficient, reproducible and simple HPLC method for the analysis of bosentan, particularly with respect to the related substances formed during the synthesis.

OBJECT OF THE INVENTION

It is therefore an object of the present invention to provide a new, alternative method for analysing bosentan, its impurities and related substances, whilst avoiding the typical problems associated with the prior art methods.

A particular object of the invention is to provide a new, accurate and sensitive HPLC method for the detection and quantitation of intermediates and related substances that are formed and may remain in the batches of bosentan and/or its salts synthesised by the route disclosed in WO 2009/004374 and its priority application IN 1245/MUM/2007.

A further object is the provision of reference markers and reference standards for use in the detection of impurities designated A-E, which are formed in processes for the preparation of bosentan, in particular by the route disclosed in WO 2009/004374 and its priority application IN 1245/MUM/2007.

SUMMARY OF THE INVENTION

The current invention provides a HPLC method for analysing bosentan wherein the mobile phase comprises two or more liquids and the relative concentration of the liquids is varied to a pre-determined gradient.

The inventors have also appreciated that five impurities, designated compounds A-E, can be utilized as reference markers or reference standards for the analysis of bosentan or of pharmaceutical dosage forms comprising bosentan. The impurities A-E have not been previously disclosed in the prior art.

Accordingly a first aspect of the present invention provides a compound A having the chemical name N-[6-(2-(2-hydroxyethoxy)ethoxy)-5-hydroxy-2-(pyrimidin-2-yl)-pyrimidin-4-yl]-4-tert-butyl benzene sulphonamide and structure:

(A)

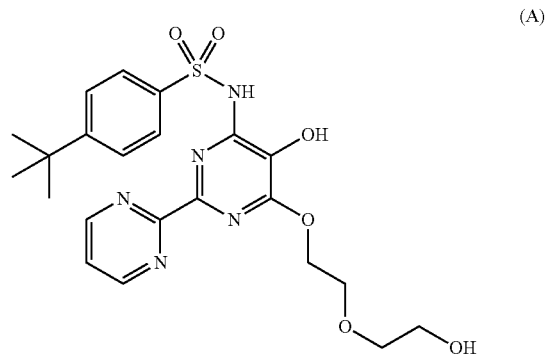 [SMILES: CC(C)(C)c1ccc(S(=O)(=O)Nc2nc(-c3ncccn3)nc(OCCOCCO)c2O)cc1]

A second aspect provides a compound B having the chemical name N-[6-(ethene-1-oxy)-5-hydroxy-2-(pyrimidin-2-yl)-pyrimidin-4-yl]-4-tert-butyl benzene sulphonamide and structure:

(B)

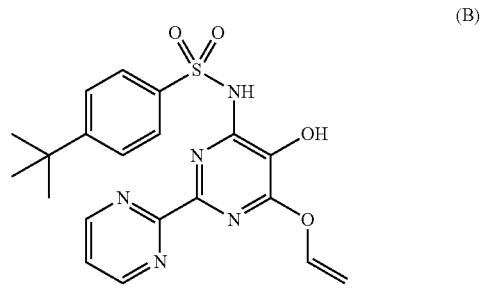 [SMILES: C=COc1nc(-c2ncccn2)nc(NS(=O)(=O)c2ccc(C(C)(C)C)cc2)c1O]

A third aspect provides a compound C having the chemical name N-[6-(2-(2-hydroxyethoxy)ethoxy)-5-(2-methoxyphenoxy)-2-(pyrimidin-2-yl)-pyrimidin-4-yl]-4-tert-butyl benzene sulphonamide and structure:

(C)

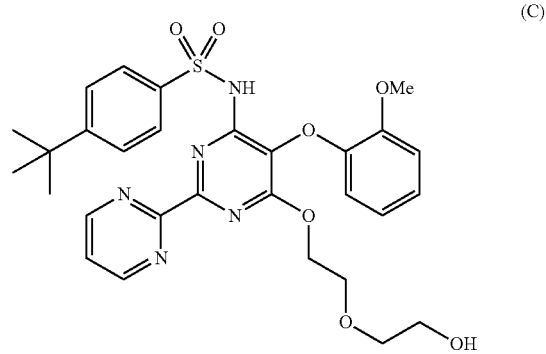 [SMILES: COc1ccccc1Oc1c(NS(=O)(=O)c2ccc(C(C)(C)C)cc2)nc(-c2ncccn2)nc1OCCOCCO]

A fourth aspect provides a compound D having the chemical name N-[6-hydroxy-5-(2-methoxyphenoxy)-2-(pyrimidin-2-yl)-pyrimidin-4-yl]-4-tert-butyl benzene sulphonamide and structure:

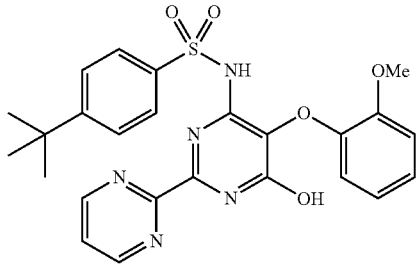

(D)

A fifth aspect provides a compound E having the chemical name N-[6-(ethene-1-oxy)-5-(2-methoxyphenoxy)-2-(pyrimidin-2-yl)-pyrimidin-4-yl]-4-tert-butyl benzene sulphonamide and structure:

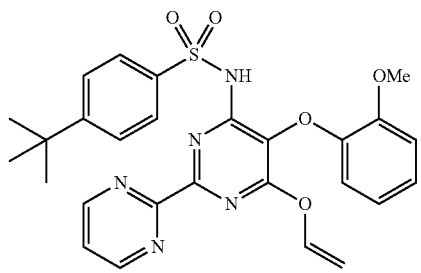

(E)

The compounds A-E, suitable for use as reference markers or reference standards, are by-products formed during the synthesis of bosentan. In a particularly preferred embodiment, the compounds A-E according to the invention are in isolated form. Most preferably, the isolated form is in substantially pure form, preferably having a purity of greater than about 90%, preferably greater than about 95%, preferably greater than about 98%, most preferably greater than about 99%, preferably as measured by HPLC.

A sixth aspect according to the invention provides a method of testing the purity of a sample of bosentan or of a pharmaceutical dosage form comprising bosentan, which method comprises assaying the sample for the presence of one or more of the compounds A-E according to the invention. In the method of the invention said compounds are acting as reference markers or reference standards.

According to a seventh aspect of the present invention, there is provided a method for the characterisation of the compounds A-E using a HPLC method for the analysis of said process impurities A-E in bosentan. Preferably, the HPLC method is a LC-MS compatible method.

Accordingly, there is provided the use of compounds A-E according to the invention as reference marker(s) or alternatively as reference standard(s) in testing the purity of a sample of bosentan or a pharmaceutical dosage form comprising bosentan.

A further aspect provides a chromatographic method for testing the purity of a sample of bosentan, said method comprising determining the presence of any one or more of compounds A-E in the sample by utilizing a reference marker or in alternative embodiments a reference standard according to the invention.

A further aspect provides a chromatographic method for testing the purity of a sample of bosentan by determining the presence of any one or more of compounds A-E in a sample comprising bosentan, said method comprising:
(a) dissolving a sample of bosentan or a dosage form comprising bosentan in a solvent to produce a sample solution;
(b) dissolving a sample of any one or more of compounds A-E in a solvent to produce a reference marker solution;
(c) subjecting the sample solution and the reference solution to a chromatographic technique; and
(d) determining the presence of any one or more of compounds A-E in the sample by reference to the presence of the known compound(s) present in the reference solution.

In one embodiment, the chromatographic method is a liquid chromatographic method such as a HPLC, LC-MS or LC-MS/MS method; preferably the chromatographic method is a HPLC method, preferably a gradient HPLC method. Alternatively the chromatographic method may be a gas chromatographic method such as GC-MS.

Preferably, the stationary phase used in the current invention is reverse phase. Suitable stationary phases include octadecylsilyl silica gel or octylsilyl silica gel.

In a preferred embodiment of the invention, there is provided a gradient HPLC method wherein the mobile phase comprises a combination of a buffer (A) and an organic solvent (B). Preferably, the buffer (A) is an aqueous buffer, preferably an aqueous solution of a phosphate salt, an acetate salt, a formate salt or trifluoroacetic acid or mixtures thereof.

More preferably, the buffer (A) is an aqueous solution of an acetate salt, most preferably ammonium acetate or alternatively ammonium formate, which in particularly preferred embodiments are present at a concentration of between about 0.01M to 1.0M.

Further preferred embodiments according to the invention provide a mobile phase wherein the organic solvent (B) is a polar protic solvent such as methanol, propanol or isopropanol, or a dipolar aprotic solvent such as acetonitrile. Preferably, the organic solvent (B) is selected from the group comprising methanol, acetonitrile, propanol or isopropanol or mixtures thereof, most preferably acetonitrile or alternatively methanol or mixtures thereof.

A particularly preferred mobile phase comprises a combination of ammonium acetate (A) and acetonitrile (B).

There is further provided a gradient HPLC method according to the invention, wherein the mobile phase comprises a gradient programming as follows:

| Time (min) | % A | % B |
|---|---|---|
| 0 | 90 | 10 |
| 40 | 10 | 90 |
| 41 | 90 | 10 |
| 50 | 90 | 10 |

A particularly preferred gradient HPLC method is also provided, wherein the mobile phase comprises ammonium acetate as the buffer (A). In another particularly preferred embodiment, the mobile phase comprises acetonitrile as the organic solvent (B).

A further preferred embodiment comprises a HPLC method wherein the pH of the buffer (A) is about 2 to 7, preferably about 2 to 6.

In other embodiments, the chromatography is carried out at a temperature of between about 15-40° C.

The HPLC method according to the current invention efficiently detects and quantifies in a single run all impurities including those selected from the following compounds.

Compound A: N-[6-(2-(2-hydroxyethoxy)ethoxy)-5-hydroxy-2-(pyrimidin-2-yl)-pyrimidin-4-yl]-4-tert-butyl benzene sulphonamide.

Compound B: N-[6-(ethene-1-oxy)-5-hydroxy-2-(pyrimidin-2-yl)-pyrimidin-4-yl]-4-tert-butyl benzene sulphonamide.

Compound C: N-[6-(2-(2-hydroxyethoxy)ethoxy)-5-(2-methoxyphenoxy)-2-(pyrimidin-2-yl)-pyrimidin-4-yl]-4-tert-butyl benzene sulphonamide.

Compound D: N-[6-hydroxy-5-(2-methoxyphenoxy)-2-(pyrimidin-2-yl)-pyrimidin-4-yl]-4-tert-butyl benzene sulphonamide Compound E: N-[6-(ethene-1-oxy)-5-(2-methoxyphenoxy)-2-(pyrimidin-2-yl)-pyrimidin-4-yl]-4-tert-butyl benzene sulphonamide.

The sample of bosentan to be tested by a method of testing the purity of bosentan according to the present invention, can be:

(a) bosentan API; or
(b) a dosage form comprising bosentan; or
(c) a bosentan salt and/or solvate (such as a hydrate); or
(d) a dosage form comprising a bosentan salt and/or solvate (such as a hydrate).

Preferably, the bosentan tested by a method of testing the purity of bosentan according to the present invention, is suitable for use in a pharmaceutical composition.

A further aspect of the present invention provides bosentan which has been subjected to a method of testing the purity of the bosentan according to the present invention. Preferably the bosentan is substantially free of one, two, three, four or all five of compounds A-E.

A further aspect of the present invention provides bosentan which is substantially free of one, two, three, four or all five of compounds A-E.

Bosentan is "substantially free" of a compound, if it comprises less than about 5% of that compound, preferably less than about 3%, preferably less than about 2%, preferably less than about 1%, preferably less than about 0.5%, preferably less than about 0.1%, preferably less than about 0.05%, preferably as measured by HPLC.

A still further aspect of the present invention provides a pharmaceutical composition comprising bosentan according to the present invention.

DETAILED DESCRIPTION OF THE INVENTION

Figure 1:
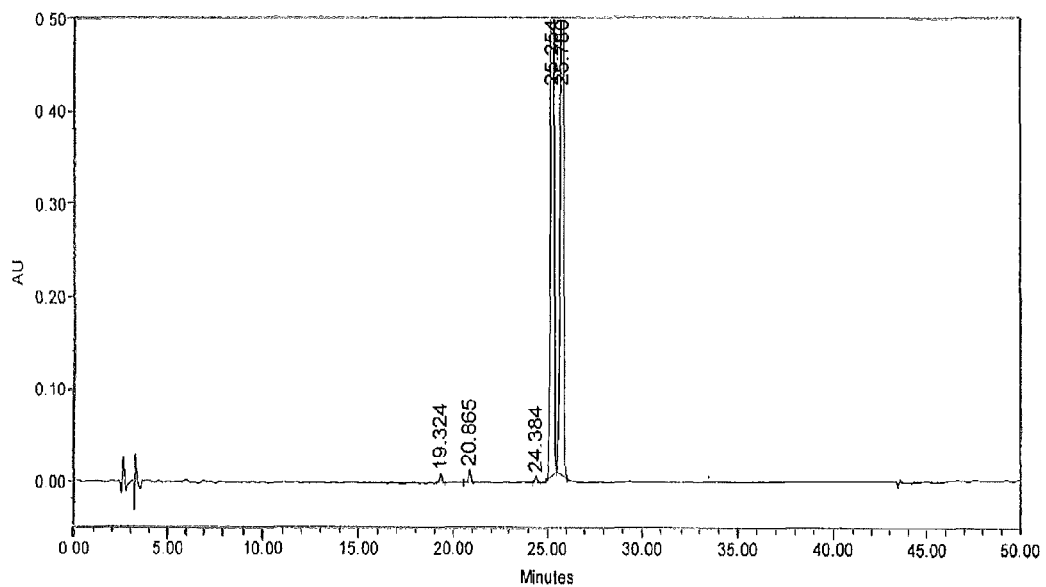
FIG. 1 shows an analytical HPLC chromatogram of sample A, analysed on a Waters instrument and represented as absorbance (absorbance units) versus time (minutes).

The current invention can be used to analyse bosentan and/or its salts as an API or bosentan and/or its salts when formulated in a pharmaceutical composition.

The pharmaceutical compositions that can be analysed by the current invention include solid and liquid compositions and optionally comprise one or more pharmaceutically acceptable carriers or excipients. Solid form compositions include powders, tablets, pills, capsules, cachets, suppositories, and dispersible granules. Liquid compositions include solutions or suspensions which can be administered by oral, injectable or infusion routes.

The term "bosentan" as used herein throughout the description and claims refers to bosentan and/or any salt or solvate (including hydrate) thereof. The current invention is particularly useful for the analysis of bosentan free base.

The terms "impurities" or "related substances" as used herein throughout the specification can mean either impurities formed in the manufacture of the API or the pharmaceutical composition and/or formed by degradation of the API or in the pharmaceutical composition on storage.

As discussed above, the HPLC methods reported in the prior art are not suitable for analysing bosentan, particularly with respect to the related substances formed in the synthesis of bosentan and/or its salts prepared by the process disclosed in WO 2009/004374 and its priority application IN 1245/MUM/2007, both of which are hereby incorporated in their entirety by reference.

However, a particularly preferred embodiment of the current invention solves this problem and efficiently detects and quantifies, in a single run, all impurities and intermediates formed in this particular synthetic process. The present invention is advantageous as the gradient method allows the elution of all polar to non-polar impurities.

The present invention is particularly suitable for determining and quantifying the presence of one or more of compounds or impurities A-E in a sample. The terms "impurity" and "compound" insofar as they relate to compounds A-E are used interchangeably herein unless described otherwise.

The current invention is also advantageous as the method is selective, sensitive, linear, precise, accurate and robust for the analysis of related substances in bosentan and/or its salts. In addition, the current invention is highly sensitive and allows detection and quantification of related substances in bosentan and/or its salts at levels much lower than acceptance limits specified by health authorities and in the ICH Guidelines.

In addition, the method of the current invention can be used to easily detect and quantify all degradation impurities formed on storage of samples of bosentan. This was established by carrying out forced degradation studies as per ICH Q1A Guidelines and validated as per ICH Q2A Guidelines covering the parameters Specificity, Linearity and Range, Precision (Repeatability, Reproducibility and Intermediate Precision), Accuracy, Limit of Detection (LOD), Limit of Quantitation (LOQ), Robustness and System Suitability.

The present inventors have developed a novel gradient HPLC method to characterise five process impurities A-E by LC-MS and LC-MS/MS. Said method is robust enough to be used in the analysis of the presence of other known related substances such as precursors in bosentan synthesis, particularly bosentan synthesised by the route described in WO 2009/004374 and its priority application IN 1245/MUM/2007. Due to large polarity differences between the impurities, precursors and bosentan, a gradient programming was considered to be most suitable by the inventors.

The inventors of the present invention have further used LC-MS and LC-MS/MS techniques to characterise the structures of new process impurities A-E.

In the working of the invention, the inventors of the present invention have found stationary phases comprising octadecylsilyl silica gel (RP-18) or octylsilyl silica gel (RP-8) to be most advantageous. A particularly preferred stationary phase comprises a Waters XTerra RP18 (250 mm×4.6 mm), 5µ, column.

The method of the current invention preferably comprises a gradient programming so that the relative concentration of the liquids A and B are typically varied to a gradient between 100% A: 0% B to 0% A: 100% B over a period of 10 to 180 minutes. Preferably, the gradient is between 100% A: 0% B to 0% A: 100% B over a period of 25 to 120 minutes, more preferably the gradient is between 100% A: 0% B to 0% A: 100% B over a period of 25 to 60 minutes, most preferably the gradient is between about 90% A: 10% B to 10% A: 90% B over about 40 minutes. The advantage of such a gradient method is that it allows the elution of all polar to non-polar impurities.

The mobile phase used is preferably selected from combinations of one or more buffer(s) (A) and one or more organic solvent(s) (B).

The buffer(s) is/are preferably selected from the group comprising an aqueous solution of a phosphate salt, an acetate salt, a formate salt or trifluoroacetic acid or mixtures thereof.

The buffer can be present at a concentration of 0.001 to 0.1 M, preferably at a concentration of 0.001 to 0.05 M, more preferably at a concentration of 0.005 to 0.05 M.

A particularly preferred mobile phase comprises a combination of ammonium acetate (A) and acetonitrile (B).

In a particularly preferred embodiment according to the invention, there is further provided a gradient HPLC method wherein the mobile phase comprises a gradient programming as follows:

| Time (min) | % A | % B |
|---|---|---|
| 0 | 90 | 10 |
| 40 | 10 | 90 |
| 41 | 90 | 10 |
| 50 | 90 | 10 |

A particularly preferred gradient HPLC method is also provided wherein the mobile phase comprises ammonium acetate as the buffer (A). In another particularly preferred embodiment, the mobile phase comprises acetonitrile as the organic solvent (B). The inventors have found that the gradient programming is particularly effective when the mobile phase comprises ammonium acetate (A) and acetonitrile (B).

The buffer (A) may contain one or more additional solvent(s) which are organic solvents selected from methanol, acetonitrile, propanol or isopropanol or a mixture thereof. The additional solvent(s) in the buffer (A) may or may not be the same solvent as the organic solvent (B). The additional solvent in the buffer (A) is preferably acetonitrile.

The pH of the buffer is selected to be between about 2 to 7.

Typically, the method of the current invention is carried out at a column temperature between approximately 15-40° C.

A further aspect of the invention provides an internal reference solution. The reference solution will comprise one or more of compounds A-E dissolved in an appropriate solvent. Said reference solution may be used in determining the presence of any of compounds A-E as impurities in a sample being analysed using chromatographic techniques according to the invention. The method of said analysis will be apparent to the skilled person.

A further aspect according to the invention provides a reference standard solution wherein a known amount of one or more of compounds A-E is dissolved in an appropriate solvent. Said reference solution may be used in determining the presence and amount of any of compounds A-E as impurities in a sample being analysed using chromatographic techniques according to the invention. The method of said analysis will be apparent to the skilled person.

The inventors have tested the methods of the current invention extensively to show that they are reproducible, accurate, precise and linear with respect to concentration and robustness.

While the present invention has been described in terms of its specific embodiments, certain modifications and equivalents will be apparent to those skilled in the art and are intended to be included within the scope of the present invention.

The present invention is illustrated but in no way limited by the following example.

EXAMPLE

HPLC Method and Analysis

The five process impurities A-E in bosentan observed during HPLC analysis were found to be above 0.1% by area normalization and are required to be identified as per ICH Q3A Guidelines. The method used for the said analysis is a gradient HPLC method according to the invention. The experimental conditions used are as follows.

Experimental Conditions:
Column: Waters XTerra RP18 (250 mm×4.6 mm), 5μ;
Flow rate: 1 ml/min;
Detection: 225 nm;
Sample concentration: 1000 ppm;
Diluent: acetonitrile;
Mobile phase: 0.03 M aqueous ammonium acetate (A)-acetonitrile (B) gradient;
The gradient program is described below:

| Time (min) | % A | % B |
|---|---|---|
| 0 | 90 | 10 |
| 40 | 10 | 90 |
| 41 | 90 | 10 |
| 50 | 90 | 10 |

Mass: API 2000 Triple Quadrapole.
Ionization mode: Positive and Negative modes.

Figure 2:
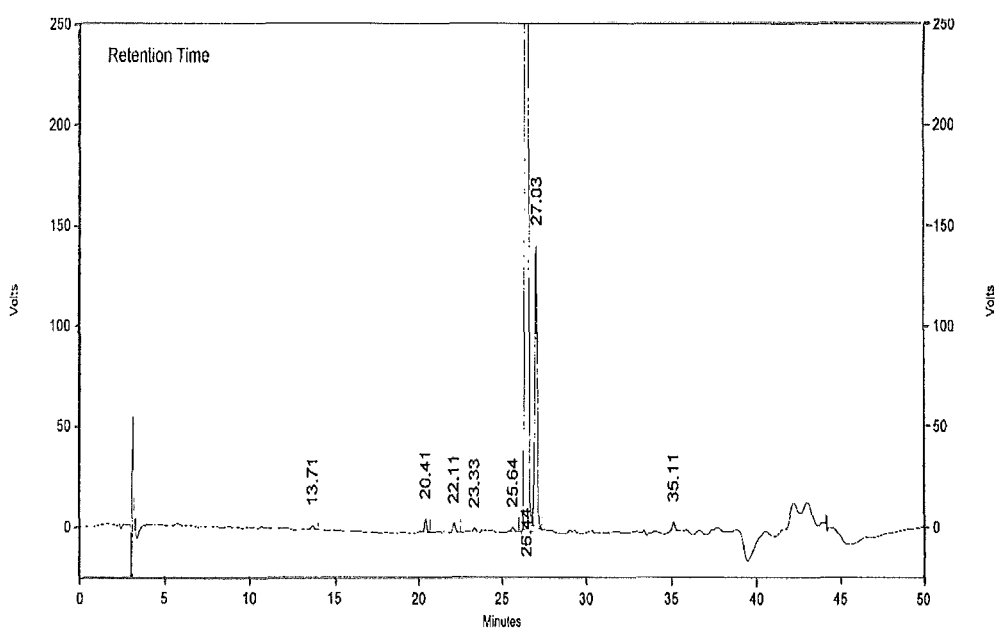
FIG. 2 shows an analytical HPLC chromatogram of sample B, analysed on a Merck Hitachi instrument and represented as voltage (volts) versus time (minutes).

Samples A and B of bosentan were analysed for process impurities by LC-MS using the above HPLC method. FIGS. 1 and 2 show the analytical HPLC chromatograms of said samples respectively.

The retention times (RT), relative retention times (RRT) and % area of each impurity by an area normalization method, molecular ions determined from the relevant mass spectra (MS) and fragments from the secondary mass spectra (MS/MS) for each impurity are summarised in Tables 1 and 2.

TABLE 1

HPLC analysis of Sample A

| Impurity | ≈RT (min) | ≈RRT | % Area | Molecular ion | Fragment ions |
|---|---|---|---|---|---|
| Bosentan | 25.25 | 1.00 | 51.77 | 552.5 $(M + H)^+$ | 508.1 |
| | | | | | 311.3 |
| | | | | | 280.4 |
| | | | | | 202.2 |
| Impurity A | 19.32 | 0.77 | 0.39 | 488.4 $(M - H)^+$ | 197.3 |
| Impurity B | 20.87 | 0.83 | 0.58 | 426.2 $(M - H)^+$ | 197.5 |
| | | | | | 173.0 |
| Impurity C | 24.38 | 0.97 | 0.28 | 594.3 $(M - H)^+$ | No diagnostic fragments |

TABLE 1-continued

HPLC analysis of Sample A

| Impurity | ≈RT (min) | ≈RRT | % Area | Molecular ion | Fragment ions |
|---|---|---|---|---|---|
| Impurity D | 25.78 | 1.02 | 46.98 | 508.4 (M + H)+ | 311.4 |
|  |  |  |  |  | 280.4 |
|  |  |  |  |  | 202.2 |

TABLE 2

HPLC analysis of Sample B

| Impurity | ≈RT (min) | ≈RRT | % Area | Molecular ion | Fragment ions |
|---|---|---|---|---|---|
| Bosentan | 26.44 | 1.00 | 92.13 | 552.5 (M + H)+ | 508.3 |
|  |  |  |  |  | 311.3 |
|  |  |  |  |  | 280.6 |
|  |  |  |  |  | 202.2 |
| Impurity A | 20.41 | 0.77 | 0.32 | 488.4 (M − H)+ | 443.2 |
|  |  |  |  |  | 334.2 |
|  |  |  |  |  | 216.3 |
|  |  |  |  |  | 196.8 |
| Impurity B | 22.11 | 0.84 | 0.23 | 426.2 (M − H)+ | 197.2 |
|  |  |  |  |  | 173.2 |
| Impurity C | 25.64 | 0.97 | 0.11 | Not detected* | Not detected* |
| Impurity D | 27.03 | 1.02 | 6.77 | 508.4 (M + H)+ | 311.2 |
|  |  |  |  |  | 280.4 |
|  |  |  |  |  | 202.2 |
| Impurity E | 35.11 | 1.33 | 0.22 | 534.7 (M + H)+ | 307.3 |

*Due to the nature of the molecule, the fragmentation was so extensive that none of the peaks were informative.

Figure 3:
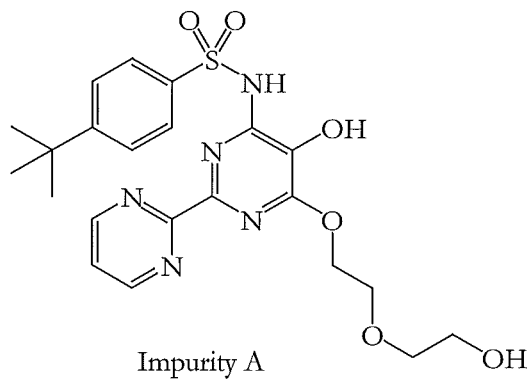
FIG. 3 shows the structures of impurities A-E.
Figure 3:
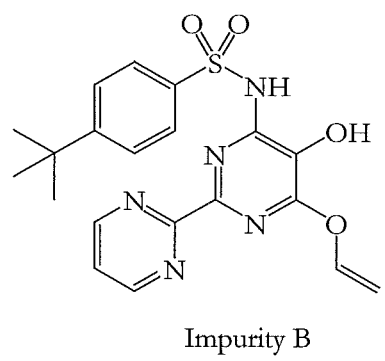
Figure 3:
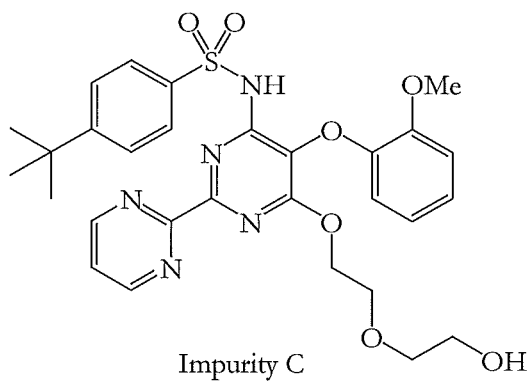
Figure 3:
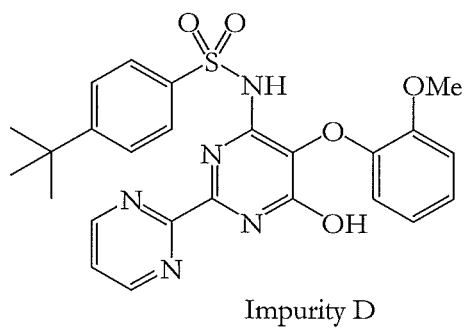
Figure 3:
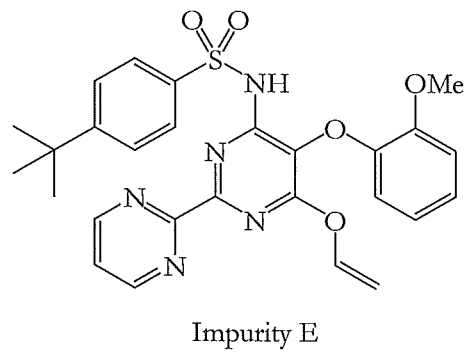
Figure 4:
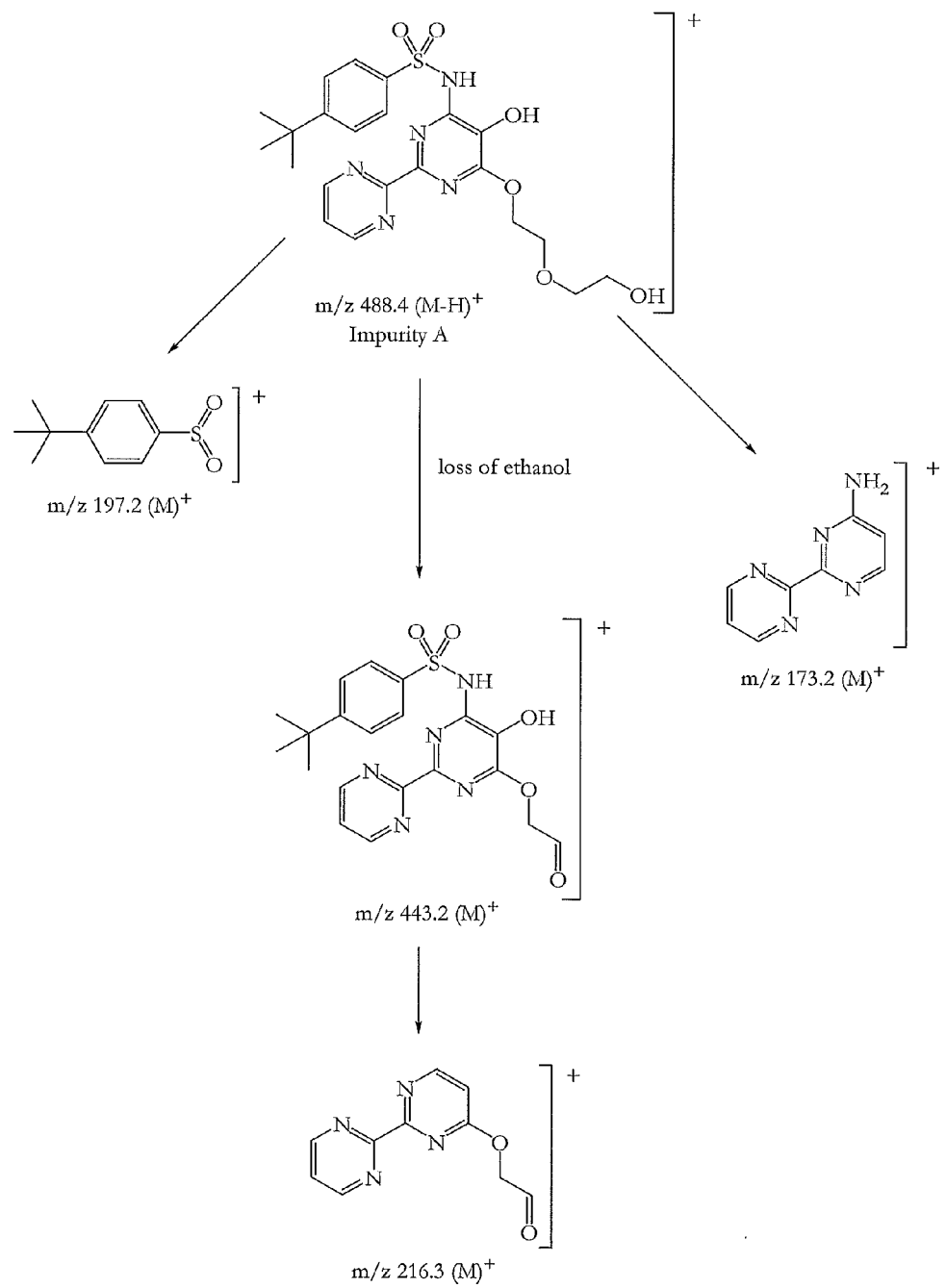
FIG. 4 shows the MS/MS fragmentation of impurity A.
Figure 5:
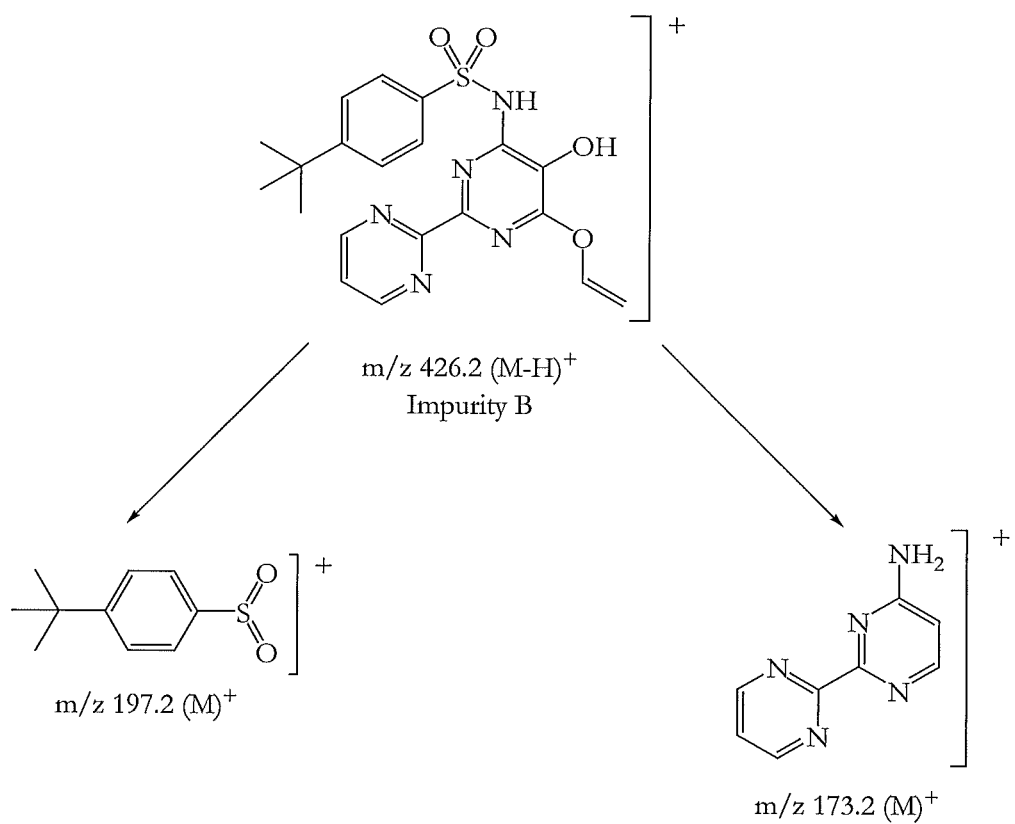
FIG. 5 shows the MS/MS fragmentation of impurity B.
Figure 6:
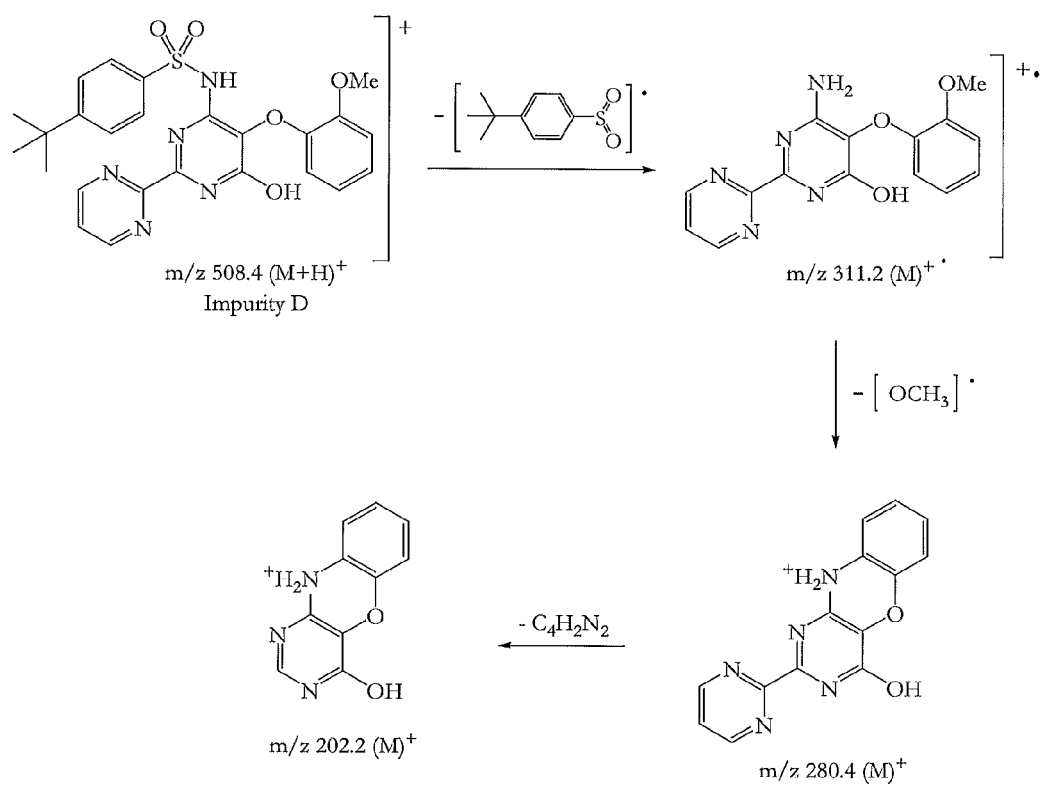
FIG. 6 shows the MS/MS fragmentation of impurity D.
Figure 7:
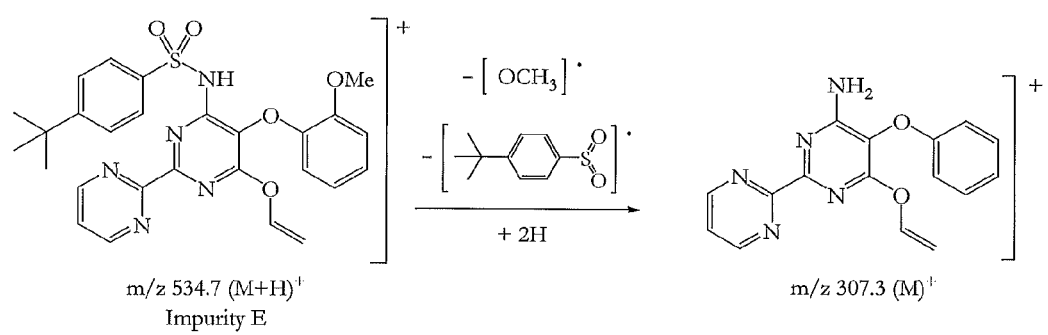
FIG. 7 shows the MS/MS fragmentation of impurity E.

Characterisation:

HPLC analysis of the samples showed impurities A-E could be detected during mass analysis. Based on the molecular ions obtained in the mass spectra of the impurities and process conditions, the structures of impurities A-E were identified as depicted in FIG. 3.

Further, on the basis of fragmentation patterns reported in the literature for bosentan (J. Am. Soc. Mass Spectrom., vol. 10(12), pages 1305-1314, 1999), the structures of the impurities A, B, D and E were confirmed by the interpretation of the fragment ions observed in MS/MS spectra. The fragmentation pattern of the impurities A, B, D and E ate shown in FIGS. 4 to 7 respectively. In the case of impurity C, the molecular ion peak observed at m/z 594.3 (M-H)+ by MS fragmented so much that during MS/MS studies none of the peaks were informative as to the nature of impurity C. Thus, due to the absence of diagnostic fragments in the MS/MS spectra of impurity C, the structural confirmation could not be performed.

The chemical names of the impurities A-E are:

Impurity A: N-[6-(2-(2-hydroxyethoxy)ethoxy)-5-hydroxy-2-(pyrimidin-2-yl)-pyrimidin-4-yl]-4-tert-butyl benzene sulphonamide.

Impurity B: N-[6-(ethene-1-oxy)-5-hydroxy-2-(pyrimidin-2-yl)-pyrimidin-4-yl]-4-tert-butyl benzene sulphonamide.

Impurity C: N-[6-(2-(2-hydroxyethoxy)ethoxy)-5-(2-methoxyphenoxy)-2-(pyrimidin-2-yl)-pyrimidin-4-yl]-4-tert-butyl benzene sulphonamide.

Impurity D: N-[6-hydroxy-5-(2-methoxyphenoxy)-2-(pyrimidin-2-yl)-pyrimidin-4-yl]-4-tert-butyl benzene sulphonamide.

Impurity E: N-[6-(ethene-1-oxy)-5-(2-methoxyphenoxy)-2-(pyrimidin-2-yl)-pyrimidin-4-yl]-4-tert-butyl benzene sulphonamide.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. An isolated compound A having the chemical name N-[6-(2-(2-hydroxyethoxy)ethoxy)-5-hydroxy-2-(pyrimidin-2-yl)-pyrimidin-4-yl]-4-tert-butyl benzene sulphonamide and structre:

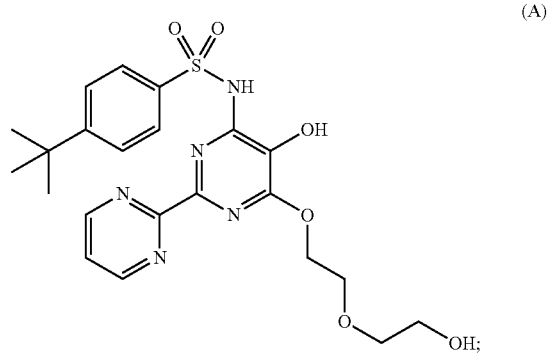 [SMILES: CC(C)(C)c1ccc(S(=O)(=O)Nc2nc(-c3ncccn3)nc(OCCOCCO)c2O)cc1]

(A)

or an isolated compound B having the chemical name N-[6-(ethene-1-oxy)-5-hydroxy-2-(pyrimidin-2-yl)-pyrimidin-4-yl]-4-tert-butyl benzene sulphonamide and structure:

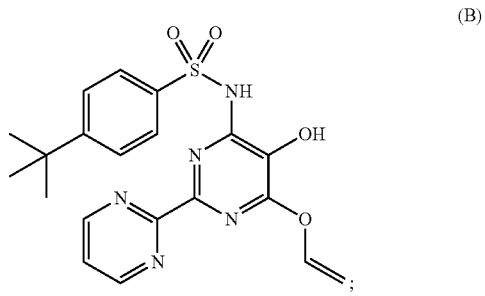 [SMILES: C=COc1nc(-c2ncccn2)nc(NS(=O)(=O)c2ccc(C(C)(C)C)cc2)c1O]

(B)

or an isolated compound C having the chemical name N-[6-(2-(2-hydroxyethoxy)ethoxy)-5-(2-methoxyphenoxy)-2-(pyrimidin-2-yl)-pyrimidin-4-yl]-4-tert-butyl benzene sulphonamide and structure:

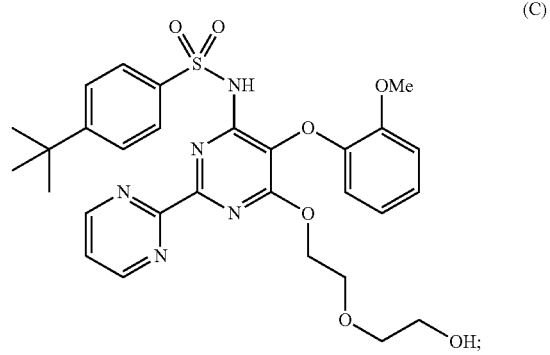 [SMILES: COc1ccccc1Oc1c(NS(=O)(=O)c2ccc(C(C)(C)C)cc2)nc(-c2ncccn2)nc1OCCOCCO]

(C)

or an isolated compound E having the chemical name N-[6-(ethene-1-oxy)-5-(2-methoxyphenoxy)-2-(pyrimidin-2-yl)-pyrimidin-4-yl]-4-tert-butyl benzene sulphonamide and structure:

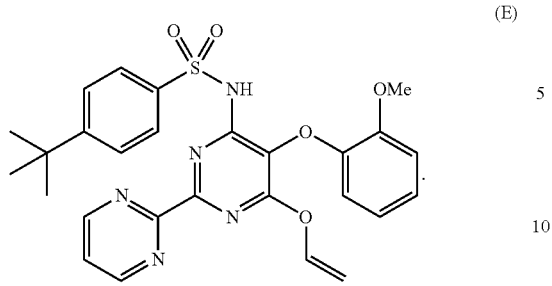

(E)

2. An isolated compound according to claim 1, which has a purity of greater than about 90%.

3. An isolated compound according to claim 2, wherein the purity is greater than about 95% as measured by HPLC.

4. An isolated compound according to claim 2, wherein the purity is greater than about 98% as measured by HPLC.

5. An isolated compound according to claim 2, wherein the purity is greater than about 99% as measured by HPLC.

* * * * *